US011571321B2

(12) United States Patent
Liu

(10) Patent No.: US 11,571,321 B2
(45) Date of Patent: Feb. 7, 2023

(54) TOE CORRECTION APPARATUS AND METHOD FOR MANUFACTURING THE SAME

(71) Applicant: BOE TECHNOLOGY GROUP CO., LTD., Beijing (CN)

(72) Inventor: Kairan Liu, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 839 days.

(21) Appl. No.: 16/458,750

(22) Filed: Jul. 1, 2019

(65) Prior Publication Data
US 2020/0008966 A1    Jan. 9, 2020

(30) Foreign Application Priority Data

Jul. 3, 2018    (CN) .......................... 201810716269.8

(51) Int. Cl.
*A61F 5/01*    (2006.01)
*A61B 5/00*    (2006.01)
*A61F 5/14*    (2022.01)

(52) U.S. Cl.
CPC ............ *A61F 5/019* (2013.01); *A61B 5/6829* (2013.01); *A61F 5/0111* (2013.01); *A61F 5/14* (2013.01)

(58) Field of Classification Search
CPC ...... A61F 5/019; A61F 5/0111; A61F 13/068; A61F 5/0113; A61F 5/0127; A61F 13/064; A61F 13/063; A61F 13/06; A61F 13/065; A61F 13/066; A61F 13/067; A61F 2/4225; A61F 5/012; A61F 5/0585; A61F 5/30; A61B 2562/0247; A61B 5/1121
See application file for complete search history.

(56) References Cited

U.S. PATENT DOCUMENTS

| 5,447,161 A * | 9/1995 | Blazek ............... A61B 5/02233 600/490 |
| 2014/0135602 A1* | 5/2014 | Lemke ................. A61B 5/0531 600/323 |
| 2018/0168840 A1 | 6/2018 | Fontaine | |

FOREIGN PATENT DOCUMENTS

| CA | 766543 A | 9/1967 |
| CN | 2721009 Y | 8/2005 |
| CN | 201085712 Y | 7/2008 |
| CN | 102564657 A | 7/2012 |
| CN | 204015256 U | 12/2014 |

(Continued)

OTHER PUBLICATIONS

First Office Action, including Search Report, for Chinese Patent Application No. 201810716269.8, dated Dec. 3, 2019, 26 pages.

(Continued)

*Primary Examiner* — Ophelia A Hawthorne
(74) *Attorney, Agent, or Firm* — Westman, Champlin & Koehler, P.A.

(57) ABSTRACT

A toe correction apparatus and a method for manufacturing the same are provided. The toe correction apparatus includes: a first sensor attachable to a first side of a hallux proximate to a second toe for measuring first pressure information between the hallux and the second toe; and a processor, configured to determine a degree to which the hallux bends to the second toe according to the first pressure information, and control an inflation amount or a deflation amount of an adjustable airbag between the hallux and the second toe according to the degree to which the hallux bends to the second toe.

20 Claims, 5 Drawing Sheets

(56) References Cited

FOREIGN PATENT DOCUMENTS

| | | |
|---|---|---|
| CN | 105054495 A | 11/2015 |
| CN | 105769408 A | 7/2016 |
| CN | 106510091 A | 3/2017 |
| CN | 107048596 A | 8/2017 |
| CN | 206390310 U | 8/2017 |
| CN | 206776866 U | 12/2017 |
| CN | 107743388 A | 2/2018 |
| CN | 207100682 U | 3/2018 |

OTHER PUBLICATIONS

Second Office Action, including Search Report, for Chinese Patent Application No. 201810716269.8, dated Jul. 14, 2020, 26 pages.

\* cited by examiner

TOE CORRECTION APPARATUS AND METHOD FOR MANUFACTURING THE SAME

CROSS-REFERENCE TO RELATED APPLICATION

The present application claims a priority to Chinese Patent Application No. 201810716269.8 filed on Jul. 3, 2018, the disclosure of which is incorporated in its entirety by reference herein.

TECHNICAL FIELD

The present disclosure relates to an apparatus for correcting hallux valgus, in particular to a toe correction apparatus and a method for manufacturing the same.

BACKGROUND

Hallux valgus is a deformity symptom in which an angle that a hallux inclines outwardly is more than 15 degrees greater than a physiological angle. The main cause of the hallux valgus is that the metatarsophalangeal joint at the bottom of the hallux is dislocated, and thus the hallux bends outwardly and a bone of the hallux protrudes outwardly. In addition to causing squeezing of deformed toes against other toes, swelling and inflammation of the hallux tends to occur at an inner side and an back portion thereof due to friction between a shoe and a foot of the user, a thick skin and a bursa is prone to be formed at an outside of the protruded bone, thereby resulting in permanent deformation of toes and continuous pain. The hallux valgus is more common in women, and a male-female ratio is about 1:40.

There are many reasons for hallux valgus, about half of which are related to genetic factors. In addition, flexibility of ligaments decreases with age, which is also one reason why the hallux valgus is more common in middle-aged and elderly women. Other common reasons leading to the hallux valgus are: a habit of wearing shoes, abnormal foot structure and joint inflammation. First, the women often wear high-heeled shoes and pointed shoes, thus the body weight wholly tends to be concentrated in the front of a foot. When pointed shoes are worn, a forefoot of the foot is squeezed in a narrow triangular area, a toe may be in an abnormal state for a long time and thus hallux valgus is caused. Second, a common type of the abnormal foot structure is flatfoot, which is prone to cause hallux valgus. Third, rheumatoid arthritis, gout and other diseases tends to destroy an abnormal balance structure of a foot soft tissue and a bone joint. The hallux valgus deformity may be caused due to the above reasons in the combined action of various internal and external factors.

SUMMARY

In an aspect, an embodiment of the present disclosure provides a toe correction apparatus, and the toe correction apparatus includes:

a first sensor attachable to a first side of a hallux proximate to a second toe, and configured to measure first pressure information between the hallux and the second toe; and a processor, configured to determine a degree to which the hallux bends to the second toe according to the first pressure information, and control an inflation amount or a deflation amount of an adjustable airbag between the hallux and the second toe according to the degree to which the hallux bends to the second toe.

In some optional embodiments, the toe correction apparatus further includes: a second sensor attachable to a second side of the hallux away from the second toe and configured to measure a second pressure information at the second side of the hallux, where the processor is configured to determine a joint protrusion degree of the hallux at the second side according to the second pressure information and control the inflation amount or the deflation amount of the airbag according to the joint protrusion degree.

In some optional embodiments, the first sensor includes an active layer, nano-paper covering the active layer, and electrodes at both ends of the active layer.

In some optional embodiments, each of the first sensor and the second sensor includes an active layer, nano-paper covering the active layer, and electrodes at both ends of the active layer.

In some optional embodiments, the nano-paper includes first nano-paper and second nano-paper, the active layer is arranged between the first nano-paper and the second nano-paper, and the active layer is made of graphene.

In some optional embodiments, the first nano-paper of the second sensor is a double-layer closed structure provided with an air hole, and the first nano-paper is configured to be an adjustable airbag by being inflated through the air hole.

In some optional embodiments, the toe correction apparatus further includes an air pump, configured to inflate the first nano-paper through the air hole to form the adjustable airbag, and to control the size of the airbag by adjusting an inflation amount or a deflation amount.

In some optional embodiments, the processor is further configured to control the air pump to inflate the first nano-paper with a first inflation amount according to the degree to which the hallux bends to the second toe and the joint protrusion degree.

In some optional embodiments, the toe correction apparatus further includes at least one of an optical sensor or an ion sensor, the optical sensor is attachable to the hallux, and configured to detect an arterial oxygen saturation of the hallux, and the ion sensor is attachable to a sole of foot, and is configured to detect a foot sweat related parameter.

In some optional embodiments, the processor is configured to determine whether the arterial oxygen saturation of the hallux is lower than a first threshold, and provide a warning in response to determining that the arterial oxygen saturation of the hallux is higher than the first threshold; or the processor is further configured to determine whether the foot sweat related parameter is higher than a second threshold, and remind the user to supplement water or electrolyte in response to determining that the sweat related parameter is higher than the second threshold.

In some optional embodiments, the first sensor is located on a first fixing band, and the second sensor is located on a second fixing band, the first fixing band is wearable on the first side of the hallux, and the second fixing band is wearable on the second side of the hallux; or the first sensor and the second sensor are respectively positioned on two sides of a first fixing member that is wearable on the hallux.

In some optional embodiments, the toe correction apparatus further includes a third sensor located on an outer surface of the first fixing member, where the third sensor and the second sensor are located on the same side of the first fixing member, and the second sensor is located on an inner surface of the first fixing member. The third sensor is configured to measure a pressure applied by a shoe onto the hallux, and the processor is configured to determine an inflation amount or a deflation amount of the airbag according to the degree to which the hallux bends to the second toe, the degree to which the joint of the hallux protrudes to the outer side of the hallux, and the pressure applied by the shoe onto the hallux.

In some optional embodiments, the toe correction apparatus further includes a third sensor attachable to an area where a shoe contacts the hallux and configured to measure a pressure applied by the shoe onto the hallux.

In some optional embodiments, the processor is on a mobile terminal communicates with the first sensor in a wireless manner.

In another aspect, an embodiment of the present disclosure provides a method for manufacturing the above toe correction apparatus, and the method includes: preparing the first sensor according to the following steps:

spraying an active material onto first nano-paper to form an active layer;

forming electrodes at two ends of the active layer respectively; and arranging second nano-paper on the active layer.

In some optional embodiments, the toe correction apparatus further includes: a second sensor attachable to a second side of the hallux away from the second toe and configured to measure second pressure information of the hallux at the second side, and the method includes forming the second sensor through the steps for preparing the first sensor.

In some optional embodiments, during preparing the first sensor, the method further includes: using nano-paper with a double-layer closed structure as the first nano-paper, and providing an air hole on the first nano-paper so that the first nano-paper is configured to be an adjustable airbag by being inflated through the air hole.

In some optional embodiments, the method further includes: installing the first sensor on a first fixing band and installing the second sensor on a second fixing band, where the first fixing band and the second fixing band are individually attachable to the hallux; or installing the first sensor and the second sensor to two sides of a first fixing member respectively, where the first fixing member is able to be worn on the hallux.

In some optional embodiments, the toe correction apparatus further includes: a third sensor, and the method further includes: forming the third sensor using the steps for preparing the first sensor, and arranging the third sensor on an outer surface of the first fixing member and on a same side of the first fixing member as the second sensor so that the third sensor is able to measure a pressure applied by a shoe onto the hallux.

DETAILED DESCRIPTION OF THE EMBODIMENTS

Specific implementations of the present disclosure will be further described hereinafter with reference to accompanying drawings and embodiments. The following embodiments are intended to illustrate the present disclosure only, but not intended to limit the scope of the present disclosure.

At present, there are two types of toe correction apparatuses. One type of toe correction apparatus is comfortable to wear, suitable for long-term wearing, but is not able to bring an obvious correction effect. The other type of toe correction apparatus is able to bring an obvious corrective effect, but it is uncomfortable to wear, therefore, a period spent on wearing this type of toe correction apparatus should be strictly controlled to be in specified time, otherwise adverse phenomena such as poor blood circulation in the wearer's foot are caused. In addition, at present, a correction force functioning on a toe of a user by a hallux valgus correction apparatus is either fixed or manually adjustable by the user. However, due to lacking of professional knowledge, the user does not know severity of hallux valgus and what strength of the correction force should be applied, thereby causing an undesirable usage effect of the hallux valgus correction apparatus.

Figure 1:
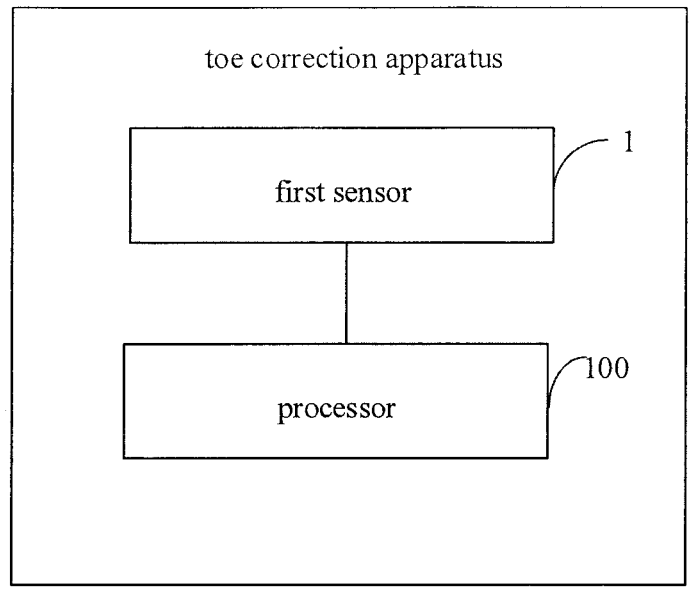
FIG. 1 is a schematic diagram of a toe correction apparatus according to an embodiment of the present disclosure.

FIG. 1 is a schematic structural diagram of a toe correction apparatus according to an embodiment of the present disclosure. As shown in FIG. 1, the toe correction apparatus includes: at least one first sensor 1 attachable to a first side of a hallux approximate to a second toe for measuring first pressure information between the hallux and the second toe; and a processor 100, configured to determine a degree to which the hallux bends to the second toe according to the first pressure information, and control an inflation amount or a deflation amount of an adjustable airbag located between the hallux and the second toe according to the degree to which the hallux bends to the second toe.

Figure 2:
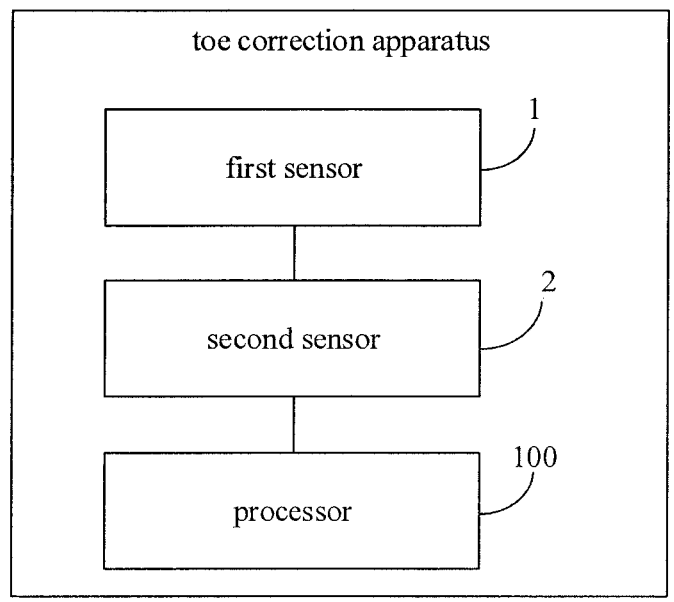
FIG. 2 is a schematic diagram of a toe correction apparatus according to an embodiment of the present disclosure.

In some optional embodiments, as shown in FIG. 2, the toe correction apparatus further includes: at least one second sensor 2, attachable to a second side of the hallux away from the second toe and for measuring second pressure information at the second side of the hallux. The processor is configured to determine a joint protrusion degree of the hallux at the second side according to the second pressure information and control the inflation amount or the deflation amount of the airbag according to the joint protrusion degree. Specifically, the at least one second sensor 2 may be arranged near or surrounding the metatarsophalangeal joint of the hallux.

In an embodiment of the present disclosure, the toe correction apparatus further includes a transceiver circuit, and the transceiver circuit is configured to transmit data collected by the first sensor 1 and the second sensor 2 to the processor. The processor is configured to determine a deformation degree of the hallux according to the data collected by the first sensor 1 and the second sensor 2.

In an embodiment of the present disclosure, the toe correction apparatus may adopt an integrated structure in which components such as a sensor, a processor are integrated locally and transmit data by wireless or wired means; or the toe correction apparatus may adopt a split structure in which components such as a sensor, and a processor are in different devices or in different positions. As an example, the processor may be located in an external device such as a computer, a tablet computer, a smart phone, and transmit data to or receive data from a sensor in a wireless communication manner; or the processor may also be located in a remote or cloud server through the base station, and data transceiving between the processor and the sensor may be achieved by relay of the base station.

In an embodiment of the present disclosure, the processor may be any logical computing device having data processing and program execution capabilities, such as a central processing unit (CPU), a field programmable logic array (FPGA), a single chip microcomputer (MCU), a digital signal processor (DSP), and an application specific integrated circuit (ASIC).

In an embodiment of the present disclosure, the wireless communication may be implemented over a wireless local area network such as Wi-Fi, Bluetooth, and Zigbee, or over a wireless wide area network such as 3G, 4G, or 5G. The wired communication method may be a cable connection such as a network cable, or an optical fiber.

When two sensors are fixed by the user on inner and outer sides of the hallux respectively, the first sensor 1 detects a degree to which the hallux inclines to the second toe, the second sensor 2 detects a degree to which a joint of the hallux protrudes towards the outer side thereof, and the processor receives data collected by the first sensor 1 and the second sensor 2 from the transceiver circuit and compares the data with predetermined data and obtain a degree to which the hallux of the user bends to the outer side of the hallux, i.e., a deformation degree of the hallux. The predetermined data may be an empirical value collected in advance, for example, may be a maximum value of a pressure experienced by the user when the user does not feel uncomfortable. When the processor is implemented by an intelligent mobile terminal of the user, detection result may be displayed to the user in real time through a display screen of the intelligent mobile terminal. For example, a user may install an application program corresponding to the toe correction apparatus of the embodiment of the present disclosure on an electronic device, since the application program may calculate and record bending degree information of the hallux according to sensed data received from the transceiver circuit, the user can intuitively obtain hallux valgus degree information of his or her own toe at present. In this way, the user can have a more intuitive understanding of a severity of his or her own disease. If the user has already experienced a treatment and correction for a period, a recovery degree of the hallux may be determined by comparing the present data with previous data.

Figure 3:
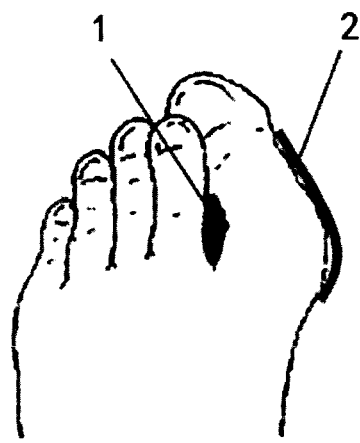
FIG. 3 is a schematic diagram of sensors of a toe correction apparatus according to an embodiment of the present disclosure.
Figure 4:
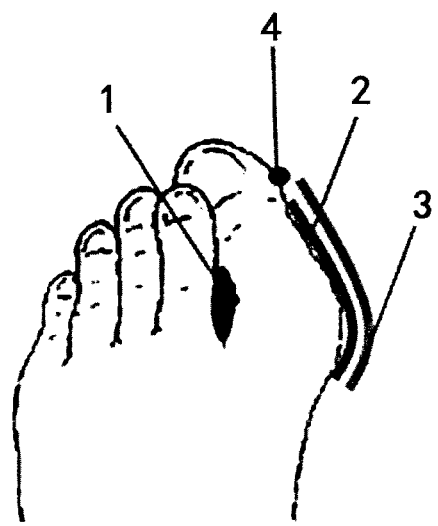
FIG. 4 is a schematic diagram of sensors of a toe correction apparatus according to an embodiment of the present disclosure.

FIG. 3 is a schematic diagram of a toe correction apparatus being worn on a foot. In some optional embodiments, the first sensor 1 is located on a first fixing band, and the second sensor 2 is located on a second fixing band, the first fixing band is wearable on the first side of the hallux, and the second fixing band is wearable on the second side of the hallux. For example, the first fixing band and the second fixing band are provided with peelable glue, and are able to be sticked onto two sides of the user's hallux respectively through the peelable glue.

In other optional embodiments, the first sensor 1 and the second sensor 2 are located on two sides of a first fixing member 200 wearable on the hallux, respectively.

Figure 5:
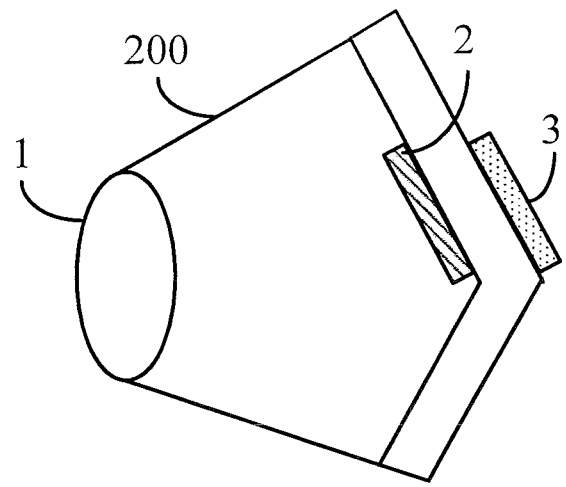
FIG. 5 is a schematic diagram of sensors of a toe correction apparatus according to an embodiment of the present disclosure.

In some optional embodiments, as shown in FIG. 5, the toe correction apparatus further includes at least one third sensor 3 located on an outer surface of the first fixing member 200 and located on a same side of the first fixing member 200 as the second sensor 2. The second sensor 2 is located on an inner surface of the first fixing member 200 for measuring a pressure between the hallux and the first fixing member 200. When the first fixing member 200 is worn on the hallux of the user, the third sensor is in contact with a shoe and is configured to measure a pressure which is applied by the shoe to the hallux. The processor is configured to determine an inflation amount or a deflation amount of an airbag according to the degree to which the hallux bends to the second toe, a degree to which the joint of the hallux protrudes to the outer side of the hallux, and the pressure which is applied by the shoe to the hallux. Optionally, the joint of the hallux is the metatarsophalangeal joint at the bottom of the hallux.

Data collected by the third sensor 3 is also sent to the processor through the transceiver circuit, and the processor is further configured to determine whether the shoe is suitable according to the determined deformation degree of the hallux and the data collected by the third sensor 3.

The long-term squeezing of the user's toes, especially the hallux, aggravates the valgus degree of the hallux of the user. The toe correction apparatus of the embodiment of the present disclosure can effectively assist the user in determining whether a shoe fits. Specifically, the processor may first calculate a level of current hallux valgus deformation degree of the user according to the data collected by the first sensor 1 and the second sensor 2, and at least predetermine a range of a maximum pressure which is able to be accepted by a foot of the user, the determination may be based on historical pressure data of the user's foot in the past or combined with network big data. The processor further determines whether the shoe meets the comfort requirement of the user's foot based on a value of a pressure which is applied by of the shoe to the hallux sensed by the third sensor 3. Similarly, when the processor is implemented through an application program in an intelligent mobile terminal, the user may obtain a determination result through the application program, or the application program may send intelligently to the user a prompt according to the determination result, thereby preventing the user from mistakenly selecting inappropriate shoes and causing more serious hallux valgus.

The toe correction apparatus according to the embodiment of the present disclosure can instruct the user how to select an appropriate shoe. Specifically, when the user tries on a shoe, the third sensor 3 detects distribution information of a pressure which is applied by the shoe onto the outer side of the hallux, especially distribution information of a pressure which is applied by the shoe onto the hallux valgus joint, and sends the distribution information to the processor through the transceiver circuit. The processor performs a comprehensively determination on distribution information of a pressure which is applied by the shoe onto the hallux of the user according to a severity degree of the user's current hallux valgus and distribution information of a pressure which is applied on the user's hallux when the hallux was in a comfortable state in the past, which is determined based on the detection data from the first sensor 1 and the second sensor 2, and obtains a determination result indicating whether the current pressure applied on the hallux is within an acceptable range and informs the determination result to the user. The user obtains the determination result through the application program and can determine whether to purchase the shoe based on the determination result, thereby simplifying a purchasing process of the user and providing convenience to the user. In addition, since each sensor detects the hallux valgus degree of the user in real time, and the processor could generates and records a detection result in real time according to the detection data, a database meeting the user's personalization, including a historical pressure distribution of the hallux and its influence can be established in the application program to provide reference for the subsequent determination of the processor. That is, the processor has machine learning capability, and the determination accuracy of the processor can gradually increase as the user's usage time increases.

Optionally, the first sensor 1, the second sensor 2 and the third sensor 3 are pressure sensors.

Figure 6:
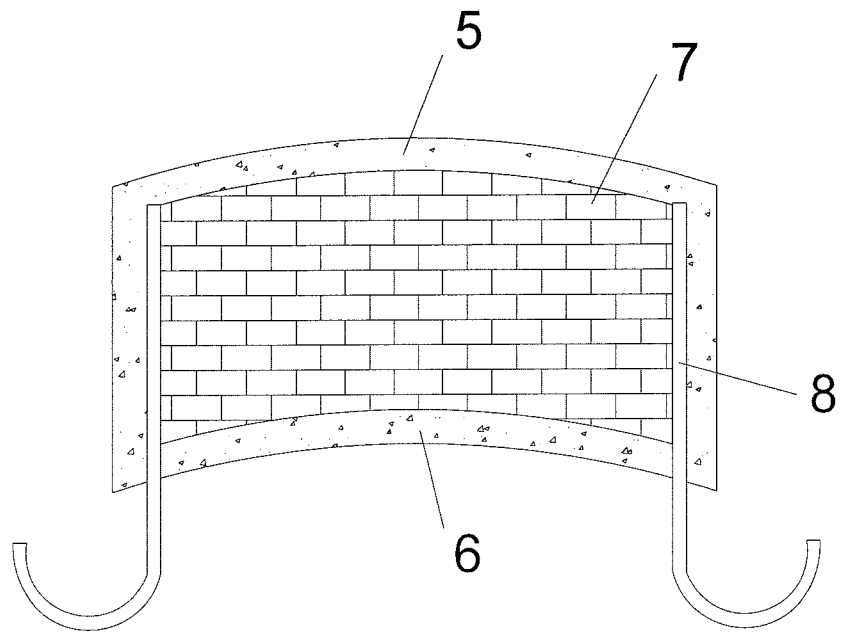
FIG. 6 is a schematic diagram of a pressure sensor of a toe correction apparatus according to an embodiment of the present disclosure.

FIG. 6 is a schematic diagram of a pressure sensor according to an embodiment of the present disclosure. As shown in FIG. 6, each of the first sensor 1, the second sensor 2, and the third sensor 3 includes an active layer 7, nano-paper 5 covering the active layer 7, and electrodes 8 respectively at two ends of the active layer 7. The nano-paper is used as a basic material, because the nano-paper has advantages such as flexibility, bio-affinity, transparency, good air permeability, which will not cause discomfort to the user when contacting with a skin of a foot of the user, and is suitable to be used as wearable products.

In some optional embodiments, the active layer 7 is made of an active material such as graphene, and the electrode 8 is made of a conductor such as copper glue. The active layer 7 includes a large number of graphene sheets. When the sensor is pressed by an external pressure, each graphene sheet is deformed, thus causing deformation of the active layer 7. In this case, the electrodes 8 sense a change in a resistance of the sensor due to the deformation of the active layer 7, i.e., a change in resistance strain. An output of the sensor represents the change in the resistance thereof. The transceiver circuit may include a measurement component that determines the output value of the sensor. The measurement unit may output a current or voltage corresponding to the change in the resistance of the sensor as a measurement value. The processor determines a magnitude of pressure applied on the sensor by calculating or looking up a table based on the measurement value received from the transceiver circuit.

Figure 7:
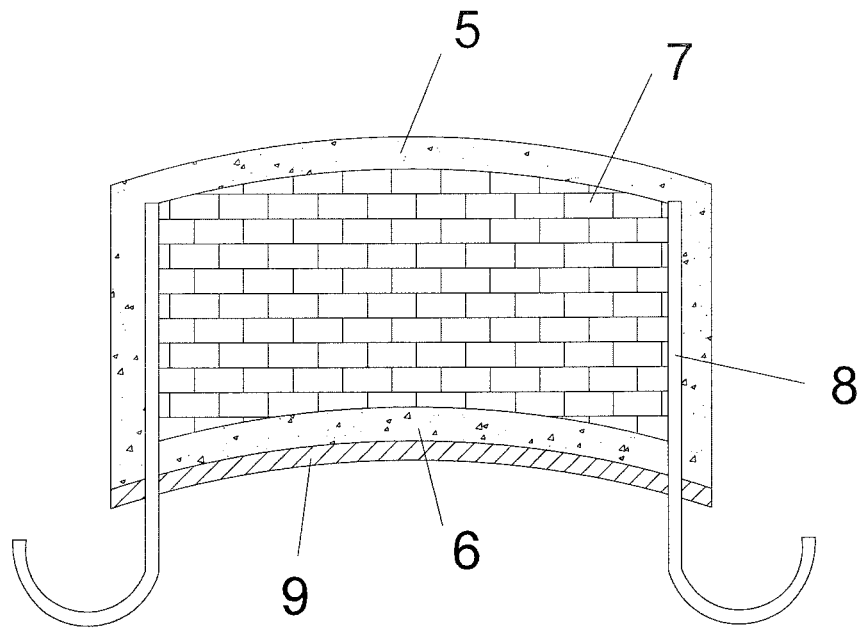
FIG. 7 is a schematic diagram of a pressure sensor of a toe correction apparatus according to an embodiment of the present disclosure.

FIG. 7 is a schematic diagram of a sensor according to an embodiment of the present disclosure. As shown in FIG. 7, the nano-paper in the sensor includes first nano-paper 5 and second nano-paper 6, in which the active layer 7 is arranged on the first nano-paper 5, and the second nano-paper 6 covers the active layer 7, so as to surround the active layer 7 together with the first nano-paper 5 to protect the active layer 7.

Figure 9:
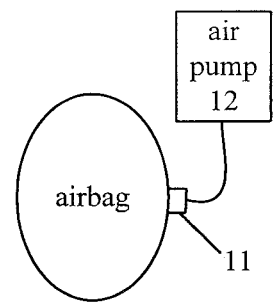
FIG. 9 is a schematic diagram of an airbag of a toe correction apparatus according to an embodiment of the present disclosure.

In an optional embodiment of the present disclosure, as shown in FIG. 9, the second nano-paper 6 in the first sensor 1 is a double-layer closed structure provided with an air hole 11, and the first nano-paper is configured to be an adjustable airbag through the air hole 11. A size of the airbag is adjustable depending on an actual hallux valgus degree of the user. When the first sensor 1 is attached to a side of the user's hallux proximate to the second toe, the inflatable airbag in the first sensor 2 is able to push the hallux to move in a direction away from the second toe, so as to urge the hallux to be reset and correct the hallux valgus.

In some optional embodiments, the toe correction apparatus further includes an air pump 12, which is configured to inflate the first nano-paper through the air hole 11 to form the adjustable airbag, and to control the size of the airbag through an inflation amount or a deflation amount.

In some optional embodiments, the processor is configured to control an inflation amount of the first nano-paper from the air pump 12.

Each element in the toe correction apparatus may be designed according to actual conditions, and an operation manner thereof may be designed as a manual control manner, a semi-automatic control manner and a full-automatic control manner. In some optional embodiments, in the manual control manner, the user manually controls the inflation amount through the air pump (e.g., an air pump) according to the pressure value displayed on the mobile phone.

In some optional embodiments, in the semi-automatic control manner, the user uses an electric air pump to control the inflation amount according to the pressure value displayed on the mobile phone.

In some optional embodiments, in the fully automatic control manner, the processor generates a target air pressure value of the airbag according to the measured pressure value, calculates an air pressure value to be adjusted according to the measured or recorded current air pressure value of the airbag, and control the electric air pump to automatically perform an inflation process to achieve the air pressure value to be adjusted.

The nano-paper is compounded by a polymer, and a nano particle or a nano cellulose.

In some optional embodiments, the number of each of the first sensor 1, the second sensor 2 and the third sensor 3 may be more than one, and each distribution of the first sensors, and the second sensors and the third sensors may be customized according to the foot type of the user. Multiple sensors form a sensor array, so that measurement result can be more accurate.

In some optional embodiments, a specific method for fixing each sensor is not unique, for example, the first sensor 1, the second sensor 2 and the third sensor 3 may be jointly arranged on a fixing member. The fixing member is able to be worn on the user's hallux or foot, and specifically may be a toe sleeve or a sock sleeve, etc. A position where the first sensor 1 is fixed depends on a specific structure of the fixing member, the first sensor 1 may be arranged on an inner side of the fixing member or on an outer side of the fixing member, and the third sensor 3 may be arranged on the outer side of the fixing member so as to be in contact with an inner side of the shoe.

In some optional embodiments, sensors may be individually fixed. As shown in FIG. 7, an adhesive layer 9 is provided on each sensor, so that each sensor is able to be individually attached to the user's toes or socks through the adhesive layer 9.

It should be noted that the second sensor may be arranged near the metatarsophalangeal joint, or an array of multiple second sensors may be arranged around the metatarsophalangeal joint.

In some optional embodiments, each sensor may be fixed to one fixing member. As shown in FIG. 5, the first sensor 1 and the second sensor 2 are respectively located on two sides of the first fixing member 200 wearable on the hallux. The second sensor 2 and the third sensor 3 are located on a same side of the first fixing member 200, the second sensor 2 is located on an inner surface of the first fixing member 200 for measuring a pressure between the hallux and the first fixing member 200, and the third sensor 3 is located on an outer surface of the first fixing member 200 for measuring the pressure between a shoe and the first fixing member 200.

Figure 8:
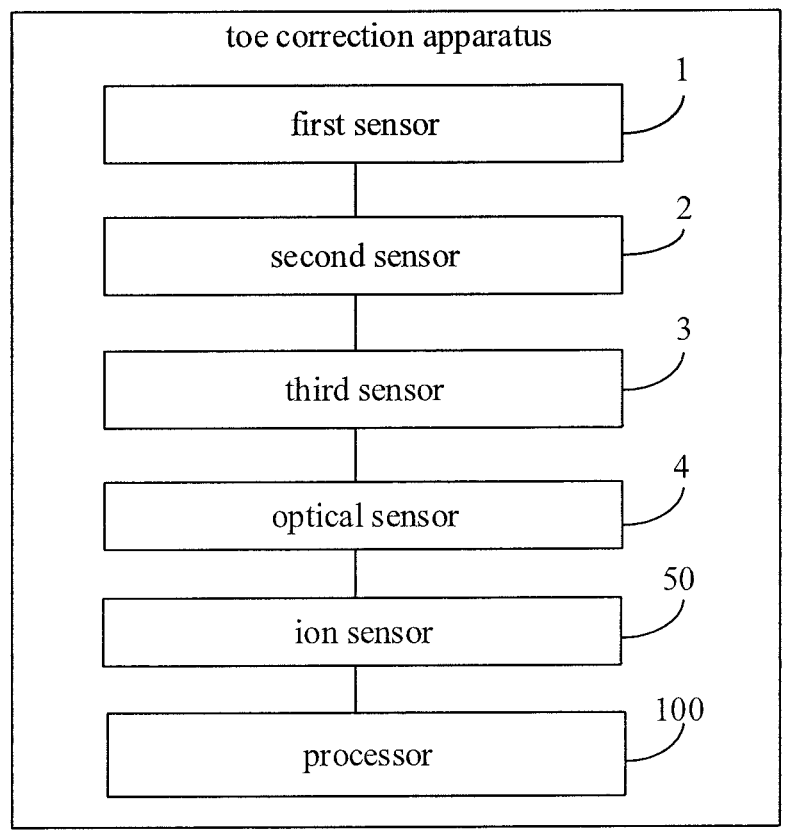
FIG. 8 is a schematic diagram of a toe correction apparatus according to an embodiment of the present disclosure.

In some optional embodiments, as shown in FIG. 8, the toe correction apparatus further includes at least one of: an optical sensor 4 attachable to the hallux and configured to detect arterial oxygen saturation of the hallux, and an ion sensor 50 attachable to a sole of the foot and configured to detect a foot sweat related parameter.

In some optional embodiments, the processor 100 is configured to determine whether the arterial oxygen saturation of the hallux is lower than a first threshold, and to provide a warning to the user in a case that it is determined that the arterial oxygen saturation of the hallux is higher than the first threshold; or the processor 100 is further configured to determine whether the foot sweat related parameter is higher than a second threshold, and remind the user to supplement water or electrolyte in a case that it is determined that the sweat related parameter is higher than the second threshold.

When the user's toe is squeezed for a long time, such as in a case that the user is wearing high-heeled shoes or pointed shoes for a long time, blood circulation of the foot of the user becomes slow, and insufficient oxygen supply will occur, thereby resulting in a low arterial oxygen saturation. In the embodiment of the present disclosure, the optical sensor 4 is configured to detect an arterial oxygen saturation of the hallux, and to remind the user to take a rest in a case that the detected arterial oxygen saturation is lower than a first threshold. For example, when the arterial oxygen saturation is lower than 90%, the optical sensor 4 reminds the user to take a rest to avoid a serious deformation of the toe. The optical sensor 4 detects and tracks the blood oxygen saturation of the user based on a photoplethymograph method.

In the embodiment of the present disclosure, the ion sensor 50 is configured to detect a PH value, contents of lactic acid, potassium ion, sodium ion through detecting the sweat components of the user, to evaluate a fatigue degree and a physical state of the user. When the sweat related parameter indicates that the user is too tired, the user can be reminded to take a rest properly and supplement water or electrolyte, etc.

Optionally, the optical sensor 4 and the ion sensor 50 may use existing chips or may be manufactured based on the related technologies.

Optionally, the processor is located on a mobile terminal, which is able to wirelessly communicate with the first sensor through a network interface. The mobile terminal includes a display screen, configured to display measurement information of each sensor to the user so as to facilitate the user to know a health state of the foot of the user in real time.

In some optional embodiments, the processor 100 analyzes hallux information collected by the five sensors, displays the analyzed hallux information on the display screen, and determines and control the inflation amount or deflation amount of the airbag according to the degree to which the hallux bends to the second toe, a degree to which the joint of the hallux protrudes towards to an outer side of the hallux, a pressure applied to the hallux by the shoe, an arterial oxygen saturation, and a sweat related parameter.

As an example, a maximum value of pressures detected by the first sensor 1, the second sensor 2, and the third sensor 3 is taken as a target pressure value, and the processor determines and controls a target inflation amount or deflation amount of the airbag based on the target pressure value.

Figure 10:
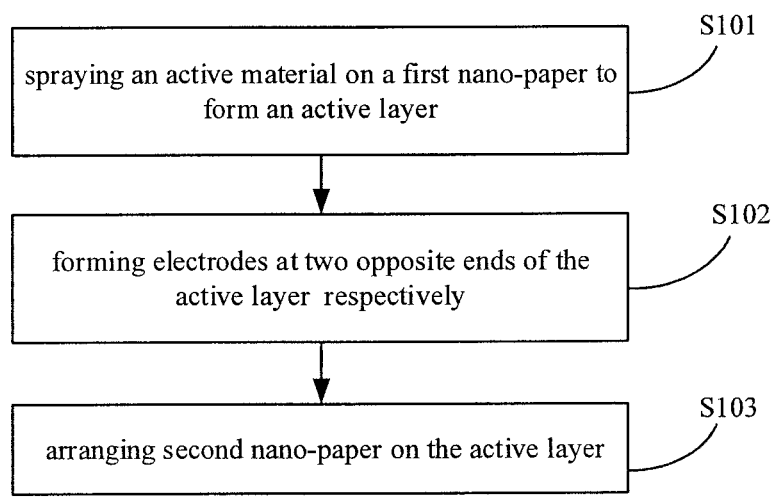
FIG. 10 is a flow chart of a method for manufacturing a toe correction apparatus according to an embodiment of the present disclosure.

FIG. 10 is a flow chart of a method for manufacturing the above-mentioned toe correction apparatus according to an embodiment of the present disclosure. As shown in FIG. 10, the method includes: preparing a first sensor 1 according to the following steps S101 to S103, specifically:

S101, spraying an active material on a first nano-paper 5 to form an active layer 7;

S102, forming electrodes 8 at two opposite ends of the active layer 7 respectively; and S103, arranging second nano-paper 6 on the active layer 7.

After the preparation of the first sensor 1 is completed, an output terminal of the first sensor 1 is connected to a power supply.

The active material in the embodiment of the present disclosure may be graphene, and the electrode 8 may be copper glue, or other materials, which is not limited herein. Specifically, in the embodiment of the present disclosure, the nano-paper is used as a basic material, because the nano-paper has advantages such as flexibility, bio-affinity, transparency, etc., which will not cause evident discomfort to the user when contacting with a skin of a foot of the user and is suitable to be used to wearing products. Since the active layer 7 made of graphene includes a large number of graphene sheets pressed against each other, when the sensor are pressed by an external pressure, each graphene sheet is deformed the external pressure, thus causing deformation of the active layer 7. In this case, the electrodes 8 sense a change in a resistance of the sensor due to the deformation of the active layer 7, i.e., a change in resistance strain. An output of the sensor represents the change in the resistance thereof. The transceiver circuit may include a measurement component that determines the output value of the sensor. The measurement unit may output a current or voltage corresponding to the change in the resistance of the sensor as a measurement value. The processor determines a magnitude of pressure applied on the sensor by calculating or looking up a table based on the measurement value received from the transceiver circuit.

In an embodiment of the present disclosure, during preparing the first sensor 1, step S103 further includes: using nano-paper with a double-layer closed structure as the first nano-paper 5, and providing an air hole on the first nano-paper 5 so that the first nano-paper is able to configured to be an adjustable airbag by being inflated through the air hole 10. When the first sensor 1 is arranged between the hallux and the second toe of the user, the hallux is able to be pushed to move in a direction away from the second toe, so as to urge the hallux to be reset and correct the hallux valgus.

In an embodiment of the present disclosure, the method includes installing the first sensor on a first fixing band and installing the second sensor on a second fixing band, where the first fixing band and the second fixing band are attachable to the hallux; or installing at least one first sensor and the second sensor to two sides of a first fixing member respectively, the first fixing member is able to be worn on the hallux.

As shown in FIG. 5, a position for fixing the first sensor 1 depends on a specific structure of the fixing member 200, and the first sensor 1 may be provided on an inner side surface of the fixing member 200 or on an outer side surface of the fixing member 200.

In an embodiment of the present disclosure, each sensor may also be fixed individually. Specifically, an adhesive layer 9 (as shown in FIG. 7) may be provided on each sensor, so that each sensor is attachable to the user's toes or socks through the adhesive layer 9. Furthermore, it is also possible to provide the adhesive layer 9 on only one or two sensors. In addition, the first sensor 1 may be disposed on one fixing member, for example, in the form of a patch, and the second sensor may be disposed on another fixing member, for example, in the form of a patch. Optionally, both the adhesive layer 9 and the fixing member may be provided, and each sensor may be fixed to the user's foot or sock by combining the adhesive layer 9 and the fixing member. Moreover, the independent fixing of sensors can also facilitate users to only use one of the sensors or fixing members according to current requirements, thus increasing the use flexibility.

Further, the method further includes preparing a third sensor 3 prepared according to steps S101 to S103. As shown in FIG. 5, the first sensor 1, the second sensor 2 and the third sensor 3 are each mounted on a fixing member 200, which is able to be worn on the hallux or the foot. The third sensor 3 is located on an outer surface of the first fixing member 200 and located at the same side of the first fixing member 200 as the second sensor 2. Optionally, the adhesive layer 9 may be further provided on the third sensor 3 to be independently attached to an inner surface of the shoe in contact with the hallux.

Those skilled in the art will recognize that units and algorithm steps of the examples described in connection with the embodiments disclosed herein can be implemented in electronic hardware, or a combination of computer software and electronic hardware. Whether these functions are implemented in hardware or software depends on specific application and design constraints of the technical solutions. Even though those skilled in the art may use different methods to implement the described functions for each particular application, such implementation should not be considered to be beyond the scope of the present disclosure.

Those skilled in the art can clearly understand that for convenience and conciseness of description, specific working processes of the above-described systems, devices and units can refer to processes corresponding to the above-described method embodiments, which will not be repeated herein.

In the embodiments provided by the present disclosure, it should be understood that the disclosed apparatuses and methods may be implemented in other ways. For example, the apparatus embodiments described above are only schematic, and the dividing for the unit is only based on the logical function. In practice, the module or the unit may be divided in other ways. For example, multiple units or assemblies may be combined or integrated into another system, or some features may be ignored or not executed. In addition, the displayed or discussed coupling, direct coupling or communication connection may be through some interfaces, and indirect coupling or communication connection of the apparatus, or may be electric or mechanical connected.

Moreover, function units of the embodiments of the disclosure may be integrated in one processing unit, or the function units may also be separated as one unit, or two or more function units may be integrated in one unit.

In the case that the function is implemented through the software function unit and is sold and used as an individual product, the individual product may be stored in a computer readable storage medium. Based on such understanding, the essence of the technical solution of the disclosure, a part of the disclosure contributing to conventional technologies may be embodied as a software product which is stored in a storage medium and includes multiple instructions for instructing a computer device (which may be a personal computer, a server, network equipment or the like) to perform all of or part of the steps of the methods according to the embodiments of the disclosure. The storage medium described above includes various mediums that can store a program code, such as, a U disk, a removable hard disk, a Read-Only Memory (ROM), a Random Access Memory (RAM), a magnetic disk or an optical disk.

The above embodiments are merely optional embodiments of the present disclosure. It should be noted that numerous improvements and modifications may be made by those skilled in the art without departing from the principle of the present disclosure, and these improvements and modifications shall also fall within the scope of the present disclosure.

What is claimed is:

1. A toe correction apparatus, comprising:
   a first sensor, attachable to a first side of a hallux close to a second toe, and configured to measure first pressure information between the hallux and the second toe; and
   a processor, configured to determine a degree where the hallux bends to the second toe according to the first pressure information, and control an inflation amount or a deflation amount of an adjustable airbag between the hallux and the second toe according to the degree where the hallux bends to the second toe,
   wherein the first sensor comprises an active layer, nano-paper covering the active layer, and electrodes at both ends of the active layer.

2. The toe correction apparatus according to claim 1, wherein each of the first sensor and the second sensor comprises an active layer, nano-paper covering the active layer, and electrodes at both ends of the active layer, the nano-paper comprises first nano-paper and second nano-paper, the active layer is arranged between the first nano-paper and the second nano-paper, and the active layer is made of graphene.

3. The toe correction apparatus according to claim 2, further comprising: an air pump, configured to inflate the first nano-paper through the air hole to form the adjustable airbag, and to control a size of the airbag by adjusting an inflation amount or a deflation amount.

4. The toe correction apparatus according to claim 3, wherein the processor is further configured to control the air pump to inflate the first nano-paper with a first inflation amount according to the degree where the hallux bends to the second toe and the joint protrusion degree.

5. The toe correction apparatus according to claim 2, wherein the first nano-paper of the second sensor has a double-layer closed structure provided with an air hole, and the first nano-paper is configured to be the adjustable airbag by being inflated through the air hole.

6. The toe correction apparatus according to claim 1, further comprising:
   a second sensor, attachable to a second side of the hallux away from the second toe and configured to measure a second pressure information at the second side of the hallux,
   wherein the processor is configured to determine a joint protrusion degree of the hallux at the second side according to the second pressure information and control the inflation amount or the deflation amount of the airbag according to the joint protrusion degree.

7. The toe correction apparatus according to claim 6, wherein the first sensor is located on a first fixing band, the second sensor is located on a second fixing band, the first fixing band is wearable on the first side of the hallux, and the second fixing band is wearable on the second side of the hallux; or the first sensor and the second sensor are respectively positioned on two sides of a first fixing member that is wearable on the hallux.

8. The toe correction apparatus according to claim 7, further comprising: a third sensor located on an outer surface of the first fixing member, wherein the third sensor and the second sensor are located on the same side of the first fixing member, and the second sensor is located on an inner surface of the first fixing member, the third sensor is configured to measure a pressure applied by a shoe onto the hallux, and the processor is configured to determine an inflation amount or a deflation amount of the airbag according to the degree where the hallux bends to the second toe, a degree where the joint of the hallux protrudes to the outer side of the hallux, and the pressure applied by the shoe onto the hallux.

9. The toe correction apparatus according to claim 1, further comprising at least one of an optical sensor or an ion sensor, wherein the optical sensor is attachable to the hallux, and configured to detect an arterial oxygen saturation of the hallux, and the ion sensor is attachable to a sole of foot, and configured to detect a foot sweat related parameter.

10. The toe correction apparatus according to claim 9, wherein the processor is configured to determine whether the arterial oxygen saturation of the hallux is lower than a first threshold, and provide a warning in response to determining that the arterial oxygen saturation of the hallux is higher than the first threshold; or the processor is further configured to determine whether the foot sweat related parameter is higher than a second threshold, and remind a user to supplement water or electrolyte in response to determining that the sweat related parameter is higher than the second threshold.

11. The toe correction apparatus according to claim 1, wherein the processor is on a mobile terminal that communicates with the first sensor in a wireless manner.

12. A method for manufacturing the toe correction apparatus according to claim 1, comprises preparing the first sensor according to following steps:

spraying an active material onto first nano-paper to form the active layer;

forming the electrodes at two ends of the active layer respectively; and arranging second nano-paper on the active layer.

13. The method according to claim 12, further comprising:

installing the first sensor on a first fixing band and installing the second sensor on a second fixing band, wherein the first fixing band and the second fixing band are individually attachable to the hallux; or installing the first sensor and the second sensor to two sides of a first fixing member respectively, wherein the first fixing member is able to be worn on the hallux.

14. The method according to claim 13, wherein the toe correction apparatus further comprises: a third sensor, and the method further comprises: forming the third sensor using the steps for preparing the first sensor, and arranging the third sensor on an outer surface of the first fixing member and on a same side of the first fixing member as the second sensor so that the third sensor is able to measure a pressure applied by a shoe onto the hallux.

15. The method according to claim 12, wherein the toe correction apparatus further comprises: a second sensor attachable to a second side of the hallux away from the second toe and configured to measure second pressure information of the hallux at the second side, and the method comprises forming the second sensor through the steps for preparing the first sensor.

16. The method according to claim 12, wherein during preparing the first sensor, the method further comprises:

using nano-paper with a double-layer closed structure as the first nano-paper, and providing an air hole on the first nano-paper so that the first nano-paper is able to configured to be an adjustable airbag by being inflated through the air hole.

17. A toe correction apparatus, comprising:

a first sensor, attachable to a first side of a hallux close to a second toe, and configured to measure first pressure information between the hallux and the second toe;

a processor, configured to determine a degree where the hallux bends to the second toe according to the first pressure information, and control an inflation amount or a deflation amount of an adjustable airbag between the hallux and the second toe according to the degree where the hallux bends to the second toe;

a second sensor, attachable to a second side of the hallux away from the second toe and configured to measure a second pressure information at the second side of the hallux, wherein the processor is configured to determine a joint protrusion degree of the hallux at the second side according to the second pressure information and control the inflation amount or the deflation amount of the airbag according to the joint protrusion degree, wherein the first sensor is located on a first fixing band, the second sensor is located on a second fixing band, the first fixing band is wearable on the first side of the hallux, and the second fixing band is wearable on the second side of the hallux; or the first sensor and the second sensor are respectively positioned on two sides of a first fixing member that is wearable on the hallux.

18. The toe correction apparatus according to claim 17, further comprising:

a second sensor, attachable to a second side of the hallux away from the second toe and configured to measure a second pressure information at the second side of the hallux, wherein the processor is configured to determine a joint protrusion degree of the hallux at the second side according to the second pressure information and control the inflation amount or the deflation amount of the airbag according to the joint protrusion degree.

19. The toe correction apparatus according to claim 17, wherein the first sensor comprises an active layer, nano-paper covering the active layer, and electrodes at both ends of the active layer.

20. A toe correction apparatus, comprising:

a first sensor, attachable to a first side of a hallux close to a second toe, and configured to measure first pressure information between the hallux and the second toe;

a processor, configured to determine a degree where the hallux bends to the second toe according to the first pressure information, and control an inflation amount or a deflation amount of an adjustable airbag between the hallux and the second toe according to the degree where the hallux bends to the second toe;

a second sensor, attachable to a second side of the hallux away from the second toe and configured to measure a second pressure information at the second side of the hallux, wherein the processor is configured to determine a joint protrusion degree of the hallux at the second side according to the second pressure information and control the inflation amount or the deflation amount of the airbag according to the joint protrusion degree, wherein each of the first sensor and the second sensor comprises an active layer, a nano-paper covering the active layer, and electrodes at both ends of the active layer.

\* \* \* \* \*